United States Patent

Chapman et al.

[11] Patent Number: 5,987,095
[45] Date of Patent: Nov. 16, 1999

[54] METHOD FOR DETECTING AN IMAGE OF AN OBJECT

[76] Inventors: Leroy Dean Chapman, 4 Vermont Cir., Bolingbrook, Ill. 60440; William C. Thomlinson, 32 E. Masem, East Patchogue, N.Y. 11772; Zhong Zhong, Apt. I 1131 Chaping 700 E. Loop Rd., Stonybrook, N.Y. 11790

[21] Appl. No.: 08/936,250

[22] Filed: Sep. 24, 1997

Related U.S. Application Data

[63] Continuation of application No. 08/732,613, Oct. 16, 1996.

[51] Int. Cl.$^6$ ................................................ G01N 23/04
[52] U.S. Cl. ............................ 378/70; 378/84; 378/98.12
[58] Field of Search ................................ 378/62, 70, 71, 378/84, 87, 37, 36, 98.12

[56] References Cited

U.S. PATENT DOCUMENTS

| | | | |
|---|---|---|---|
| 4,599,741 | 7/1986 | Wittry | 378/85 |
| 5,245,648 | 9/1993 | Kinney et al. | 378/43 |
| 5,259,013 | 11/1993 | Kuriyama et al. | 378/43 |
| 5,319,694 | 6/1994 | Ingal et al. | 378/84 |
| 5,579,363 | 11/1996 | Ingal et al. | 378/84 |

FOREIGN PATENT DOCUMENTS 95 05725  2/1995  WIPO .

OTHER PUBLICATIONS

Tetsuya Ishikawa, Seishi Kikuta and Kazutaka Kohra, Angle–Resolved Plane Wave X–Ray Topography, *Japanese Journal of Applied Physics*, vol. 24, No. 7, Jul., 1985, pp. L559–L562.

R.C. Blasdell and A.T. Macrander, Prototype grooved and spherically bent Si backscattering crystal analyzer for meV resolution inelastic x–ray scattering, *Review of Scientific Instruments*, vol. 66, No. 2, Feb. 1995, pp. 2075–2077, New York.

D. Chapman, W. Thomlinson, R.E. Johnson, D. Washburn, E. Pisano. N. Gmür, Z. Zhong, R. Menk, F. Arfelli and D. Sayers, *X–Ray Refraction Imaging (XRI) Applied to Mammography*, published Oct. 31, 1997.

V.N. Ingal and E.A. Beliaevskaya, *Phase Dispersion Introscopy*, (published prior to Oct. 16, 1996).

V.N. Ingal and E.A. Beliaevskaya, *Phase Dispersion Introscopy, Surface Investigation*, vol. 12, pp. 441–450, 1997.

V.A. Bushuev, V.N. Ingal and E.A. Belyaevskaya, Dynamical Theory of Images Generated by Noncrystalline Objects for the Method of Phase–Dispersive Introscopy, *Crystallography Reports*, vol. 41, No. 5, 1996, pp. 766–774.

V.A. Bushuev, E.A. Beliaevskaya and V.N. Ingal, Wave–optical description of X–ray phase contrast images of weakly absorbing non–crystalline objects, *Il Nuovo Cimento*, vol. 19D, No. 2–4, Feb.–Apr. 1997.

V.N. Ingal and E.A. Beliaevskaya, Imaging of biological objects in the plane–wave diffraction scheme, *Il Nuovo Cimento*, vol. 19D, No. 2–4, Feb.–Apr. 1997.

V.N. Ingal and E.A. Beliaevskaya, X–ray plane–wave topography observation of the phase contrast from a non–crystalline object, *J. Phys. D: Appl. Phys.* 28 (1995) 2314–2317.

V.N. Ingal and E.A. Belyaevskaya, Method of phase–dispersion introscopy, *Tech. Phys.* 42 (1), Jan. 1997.

V.N. Ingal and E.A. Beliaevskaya, Phase dispersion radiography of biological objects, *Physica Medica*, vol. X11, No. 2, Apr.–Jun. 1996.

*Primary Examiner*—David P. Porta
*Attorney, Agent, or Firm*—Pauley Petersen Kinne & Fejer

[57] ABSTRACT

A method for detecting an absorption, refraction and scatter image of an object by independently analyzing, detecting, digitizing, and combining images acquired on a high and a low angle side of a rocking curve of a crystal analyzer. An x-ray beam which is generated by any suitable conventional apparatus can be irradiated upon either a Bragg type crystal analyzer or a Laue type crystal analyzer. Images of the absorption, refraction and scattering effects are detected, such as on an image plate, and then digitized. The digitized images are simultaneously solved, preferably on a pixel-by-pixel basis, to derive a combined visual image which has dramatically improved contrast and spatial resolution over an image acquired through conventional radiology methods.

19 Claims, 6 Drawing Sheets

METHOD FOR DETECTING AN IMAGE OF AN OBJECT

This application is a continuation of a copending application Ser. No. 08/732,613 filed on Oct. 16, 1996.

This work was supported in part by U.S. Army Grant DAMD17-96-1-6143; U.S. Department of Energy Contact DE-AC02-76CH00016; and U.S. Department of Defense Advanced Research Projects Agency, ARPA Contract AOB227.

BACKGROUND OF THE INVENTION

1. Field of the Invention

This invention relates to a method for detecting an image of an object, such as one mass internal with respect to another mass wherein the one mass has an absorption content refraction content and/or scattering content different than the other mass, by separating, analyzing and combining an absolute absorption and a refraction angle which a beam experiences in traversing the object. These are then used to deduce a scatter image.

2. Description of Prior Art

X-ray imaging has been used in the medical field and for radiology in general, such as non-destructive testing and x-ray computed tomography. Conventional radiology systems use x-ray absorption to distinguish differences between different materials, such as normal and abnormal human tissues.

X-ray imaging for screening mammography has been used to identify early stages of breast cancer. It is well known that breast cancer mortality among women under screened controls can be significantly reduced when compared with unscreened controls. Mammography tends to identify smaller and less advanced stages of cancer, when compared with cancers found by breast physical examination or breast self-examination. Treatment of smaller and less advanced stages of breast cancer result in better survival rates. It is quite apparent that enhanced radiology methods can be used to detect even smaller and earlier stage breast cancers. Approximately 10% of clinically obvious breast cancers are not visible in images produced by conventional mammography methods.

In particular, breast cancer which is not visible with conventional mammography methods occurs most frequently in patients with relatively large amounts of breast glandular tissue. The density of the breast glandular tissue tends to obscure underlying pathology. Although The National Cancer Institute, The American College of Radiology and the American Cancer Society advocate annual screening mammograms for women over the age of 50, screening for women under the age of 50 is more controversial. In order to detect early stages of cancer, it is desirable to increase the sensitivity of mammography in younger women so that smaller and earlier stages of breast cancer can be detected. Earlier detection of breast cancer may result in significantly reduced mortality rates.

Mammographic technology has improved dramatically over the last two decades. For example, dedicated mammography equipment now exists with appropriate x-ray beam quality, adequate breast compression and automatic exposure control. Recently developed digital mammography is now being introduced throughout medical facilities. However, conventional mammographic technology depends upon the depiction of x-ray absorption to define differences between normal and abnormal tissues.

Ingal et al., U.S. Pat. No. 5,319,694 discloses a method for obtaining an image of an internal structure of an object. Radiation transmitted through an object is collimated by a Laue type crystal analyzer. While deflecting the crystal analyzer interferogram images of the internal structure of the object are monitored and a position of the crystal analyzer which provides an image with maximum contrast is selected. Both the transmitted beam and the diffracted beam emerging from the crystal analyzer carries information on the internal structure of the object. Simultaneous observation of the object in both the transmitted beam and the diffracted beam allows detection of artifacts in the image. Once the image is detected, the crystal analyzer is set to a position at which the maximum contrast of the object image is attained.

According to U.S. Pat. No. 5,319,694, simultaneous registering of images in a transmitted beam and a diffracted beam enables definition of minor and low-contrast image elements and elimination of errors in interpretation of the image due to the imperfection of the image detector. Algebraic addition of the transmitted image and the diffracted image enhances the contrast of the boundaries between different-density media, which is due to elimination of background resulting from photoelectric absorption of radiation in the object. A detector that detects the diffracted beam has a feedback loop output which is connected to a precision displacement actuator which moves the crystal analyzer.

There is an apparent need for mammographic and radiologic methods that can be used to detect even smaller and earlier stages of breast cancer, than the stages of breast cancer that can be detected with conventional imaging technology.

SUMMARY OF THE INVENTION

It is one object of this invention to provide a method for detecting an image of an object and using the image to determine differences in composition of matter and/or structural arrangement of the object.

It is another object of this invention to provide a method for detecting an image which is nearly scatter-free, by determining and combining both the absolute absorption and the refraction effects resulting from x-rays traversing the object.

It is yet another object of this invention to detect and then digitize a combined absolute absorption and refraction image at two points on a rocking curve of a crystal analyzer and then to use both digitized images to solve for and derive a combined image of an object.

The above and other objects of this invention are accomplished with a method that irradiates an x-ray beam, such as a mono-energetic synchrotron beam, through an object and directs a transmitted beam, which is emitted from the object, at an angle of incidence upon a crystal analyzer, such as a Bragg type crystal analyzer or a Laue type crystal analyzer. A diffracted beam emitted from the crystal analyzer is used to detect a refraction image of the object. An absolute absorption image of the object is also detected. The refraction image and the absolute absorption image is detected at two positions of the crystal analyzer and then both images are arithmetically solved to derive a combined image of the object which is nearly scatter-free. The method of this invention results in significantly enhanced clarity of the image of the object. Furthermore, when this is applied using a Laue type analyzer, a transmitted beam image is also acquired. When images are taken on both sides of the rocking curve, this results in four images. The diffracted beam images can be combined to give a refraction and an absorption image as with the Bragg type analyzer. This information can be used in combination with the transmitted beam images to deliver an image of only the scatter of the object.

The imaging method according to this invention can be referred to as an X-ray Refraction Imaging (XRI) method which can be used to independently detect, analyze, combine and visualize the refraction, absorption and scattering effects upon an image of an object. The method of this invention is particularly useful for relatively thick and thus highly absorbing materials. The XRI method according to this invention uses a synchrotron mammography imaging technique which has relatively high intensity and collimation of synchrotron radiation to create a mono-energetic line scan imaging system which has relatively little scatter. Earlier experiments performed according to the method of this invention revealed that the XRI method of this invention is sensitive to refractive index effects within an object being imaged, as well as being sensitive to the absorption effects of the object.

Once the absolute absorption image and the refraction image of the object are digitized, a relatively simple algorithm can be used to independently determine refractive index effects and absorption effects. The digitized images provide an absolute absorption image, which is the normal result of conventional radiography, and a refraction image resulting from the form of the angle through which the x-rays deviate in traversing the object. The method according to this invention has proven to work with either a Laue type crystal analyzer which allows a further processing to give a scatter image, which is a transmission type analyzer, or a Bragg type crystal analyzer, which is a reflection type analyzer.

The XRI method according to this invention does not depend upon phase contrast to determine the image of an object. Rather, the XRI method according to this invention depends upon an algorithm to reduce the images into separated refraction effects and absorption effects.

BRIEF DESCRIPTION OF THE DRAWINGS

The above-mentioned and other features and objects of this invention will be better understood from the following detailed description taken in conjunction with the drawings wherein.

DESCRIPTION OF PREFERRED EMBODIMENTS

Figure 1:
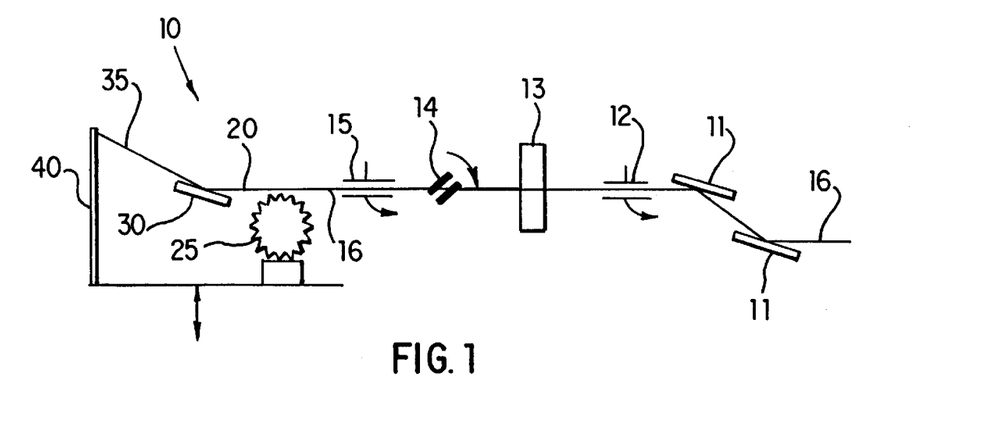
FIG. 1 is a schematic diagram of a crystal analyzer system setup with a Bragg type crystal analyzer, according to one preferred embodiment of this invention.

FIG. 1 shows a schematic diagram of analyzer system 10, according to one preferred embodiment of this invention. Crystal analyzer 30, as shown in FIG. 1, represents a Bragg type crystal analyzer. It is apparent that a Laue type analyzer can also be used to produce the same result of generating diffracted beam 35, for analysis purposes.

The double crystal monochromator 11 can be used to generate x-ray beam 16, such as a mono-energetic synchrotron beam. Each crystal of monochromator 11 is preferably constructed of silicon using a (3, 3, 3) lattice planes structure. The lattice planes used in monochromator 11, such as the (3, 3, 3) lattice planes, should preferably match those used in crystal analyzer 30. Through experimentation, the (3, 3, 3) lattice planes structure increased the sensitivity to refraction effects by a factor of about 5, when compared to experiments conducted with (1, 1, 1) lattice planes structure. According to one preferred embodiment of this invention, x-ray beam 16 has an energy level in a range of approximately 16 keV to approximately 25 keV, and preferably approximately 18 keV, with a bandwidth of approximately 1.5 eV.

In one preferred embodiment according to this invention, x-ray beam 16 is approximately 80 mm wide and approximately 0.1 mm high. Shutter 14, such as a rotary shutter or the like, can be used to control exposure and limit unnecessary scatter.

Any suitable detector known to those skilled in the art can be used to detect an image of object 25. In one preferred embodiment according to this invention, the object 25 image is detected with image plate which comprises a photostimulable phosphor image plate typically used for radiology, such as FUJI Medical Systems high resolution HR5 and standard resolution ST5 image plates. An image recorded on image plate 40 can be digitized, stored and displayed, for example by a FUJI Medical Systems AC3 reader and workstation or by any other suitable digital conversion means known to those skilled in the art. A suitable spatial resolution of images can be 0.1×0.1 mm².

Figure 11:
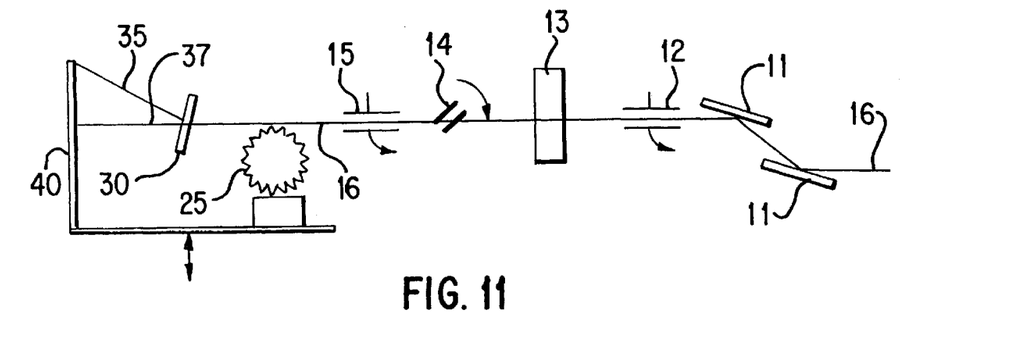
FIG. 11 is a schematic diagram of a crystal analyzer system setup with a Laue type crystal analyzer, according to another preferred embodiment of this invention.

According to one preferred embodiment of this invention, object 25 and image plate 40 or another suitable detector can be scanned together, such as in a direction shown by the vertical arrow in FIGS. 1 and 11, to provide a two-dimensional radiograph. Such scanning can be accomplished, for example by a computer controlled stepper motor translation stage which holds a support for object 25 and which also holds an image plate cassette.

Ionization chamber 12 can be used downstream of monochromator 11, for example to monitor tuning. Ionization chamber 15, as shown in FIG. 1, which is positioned upstream of object 25, can be used to monitor a radiation dose at a surface of object 25.

Crystal analyzer 30 is preferably positioned between object 25 and image plate 40. Crystal analyzer 30 is preferably fixed spatially with respect to transmitted beam 20, oriented to diffract transmitted beam 20 onto image plate 40. Fine angular control of crystal analyzer 30 can be accomplished with a stepper motor driven translation stage pushing on a relatively long rod which is mechanically connected to an axle onto which crystal analyzer 30 is attached. The fine angular control may result in a resolution limit of approximately 1 microradian. Such fine tuning can position crystal analyzer 30 at various positions within the rocking curve, as shown in FIG. 2.

Figure 3:
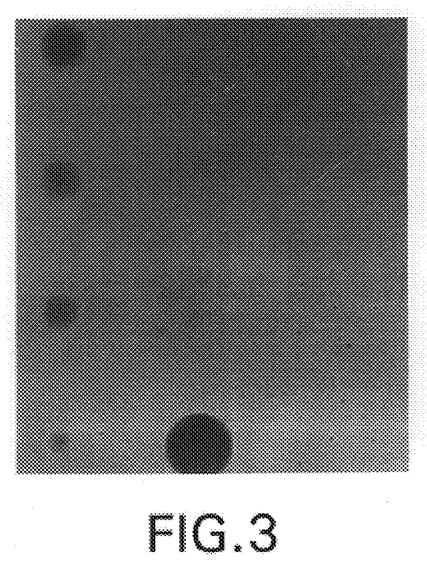
FIG. 3 is a photograph of an image taken of an ACR phantom, at a low rocking curve angle of the crystal analyzer.
Figure 4:
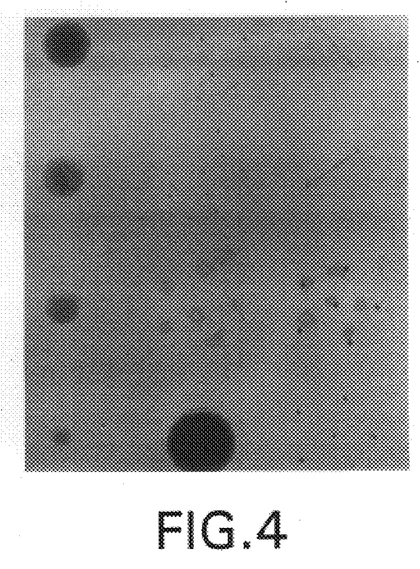
FIG. 4 is a photograph of an image taken of the same ACR phantom, at a high rocking curve angle of the crystal analyzer.

A standard test object or phantom which is used for quality control in mammography is an American College of Radiology (ACR) Mammography phantom, which is manufactured by Gammex RMI, Model 156, and known to those skilled in the art. The ACR phantom contains objects which simulate features presented by lesions in breast tissue, such as masses, fibrils and specks. Experiments conducted according to the method of this invention used skin entry doses delivered to the phantom which are within a range of acceptable dose values for human breast imaging, such as approximately 100 microrads. FIGS. 3 and 4 show actual images of the ACR phantom acquired according to the method of this invention. FIG. 3 shows an image $I_L$ of the ACR phantom, taken at a low rocking curve angle of crystal analyzer 30. FIG. 4 shows an image $I_H$ of the ACR phantom, taken at a high rocking curve angle of crystal analyzer.

Both images $I_L$ and $I_H$ have a similar absorption content, but a sensitivity to refraction effects is reversed between both images $I_L$ and $I_H$. A sensitivity to refraction occurs because crystal analyzer 30 has a relatively steep intensity versus angle dependence. The intensity as a function of a crystal angle curve is called the rocking curve. For example, the rocking curve for the reflection of the silicon with a (3, 3, 3) lattice structure at an imaging energy level of 18 keV is shown in FIG. 2, for a Bragg type crystal analyzer 30.

Figure 2:
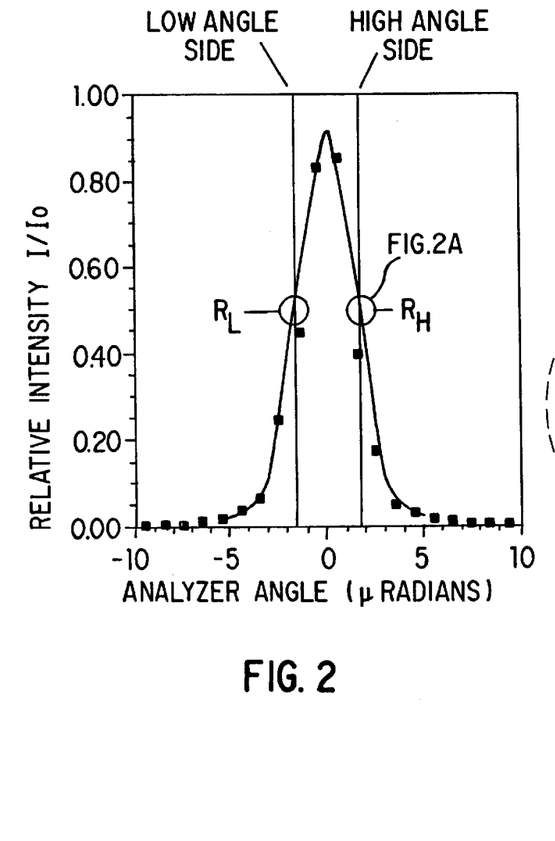
FIG. 2 is a graphical representation of an analyzer rocking curve for a silicon crystal Bragg type analyzer having (3, 3, 3) lattice planes structure at an approximately 18 keV x-ray energy level.
Figure 2A:
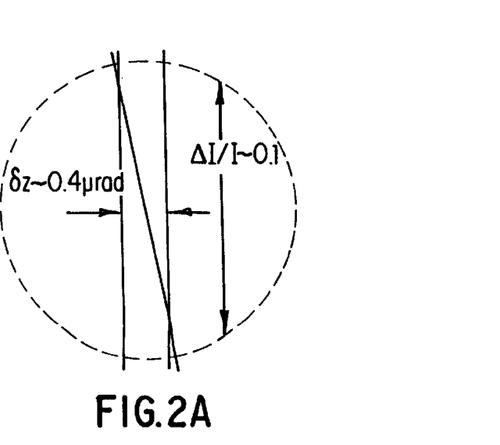

As shown in FIG. 2, the solid line curve represents a theoretical calculation of the rocking curve for crystal analyzer 30. Such theoretical calculation includes effects of x-ray beam 16, as prepared by double crystal monochromator 11. The asterisks of FIG. 2 represent measured points of the rocking curve of crystal analyzer 30, taken during an experiment conducted according to the method of this invention.

In one preferred embodiment according to this invention, the full width at half maximum (FWHM) of the rocking curve, both calculated and measured, is approximately 5 microradians. The FWHM allows a sensitivity range of refraction angle effects in an object to be approximately 2 microradians before saturation effects occur. FIG. 2 shows the low angle side and the high angle side of the rocking curve, which are preferably the locations at which both images $I_L$ and $I_H$ are detected. Close inspection of the images shown in FIG. 3 and 4 reveal that edges of features in the images are enhanced in both images, when compared to similar images detected with conventional technology. Edges of the images shown in FIGS. 3 and 4 are highlighted as if a shadow was cast on a three-dimensional surface. Such shadowing effect is reversed between both images of FIGS. 3 and 4, which is due to reversed refraction sensitivity on each side of the rocking curve.

Figure 5:
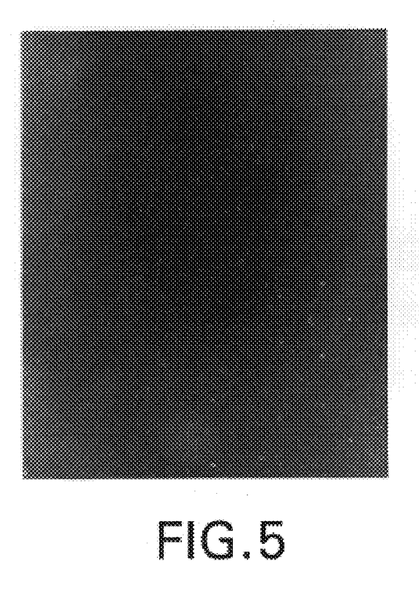
FIG. 5 is a photograph of an image taken of the same ACR phantom, with a Siemens Mammomat II, manufactured by Siemens Medical Systems in Iselin, N.J., mammography x-ray machine, operated at 24 kVp.
Figure 6:
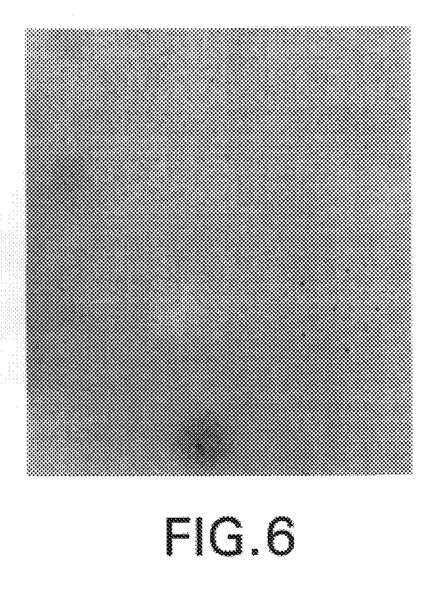
FIG. 6 is a photograph of an image taken of the same ACR phantom, using mono-energetic synchrotron radiation at 18 keV, without a crystal analyzer in place.

For comparison purposes, FIGS. 5 and 6 represent images detected with conventional radiography, of the same ACR phantom. The images shown in FIGS. 5 and 6 were taken with a conventional mammography unit, as manufactured by Siemens Mammomat II, Siemens Medical Systems, Iselin, N.J., at 24 kVp, and with mono-energetic synchrotron radiation at 18 keV, without an analyzer in place.

The two images $I_L$ and $I_H$ acquired with either a Bragg type or a Laue type crystal analyzer 30, represent independent measurements of the combined absorption and refraction properties of object 25. It should be noted that there is a distinction between refraction and scattering. Refraction occurs from long range spatial variations in a density and/or thickness of a material. In one preferred embodiment according to this invention, a range of refraction angles used in experimentation was less than approximately 1 microradian. Scattering occurs when a material is structured on a length scale comparable to an x-ray wavelength. Any ordered arrangement within object 25 that scatters x-rays with an angle greater than a few microradians will likely be rejected by crystal analyzer 30. Thus, any scattering due to order in the material of object 25 will reduce a diffracted intensity and will appear in the image as an apparent absorption. Such effect allows for image contrast based on scattering by, as well as absorption of, the material of object 25.

The arrangement of analyzer system 10 according to this invention allows a sensitivity to refraction effects along a direction in which crystal analyzer 30 diffracts transmitted beam 20. Such direction represents a scan direction which was used in experimental measurements according to one preferred embodiment of the method of this invention. Thus, according to one preferred embodiment of this invention, analyzer system 10 is sensitive to refraction effects in such direction. If such direction is arbitrarily chosen to be the z direction, then an angle of x-rays deviated by object 25 in the z direction is denoted by $\delta_z$. Such small deviation angles tend to redirect x-rays transmitted through crystal analyzer 30 and also tend to modulate an intensity diffracted by a Bragg type crystal analyzer 30, according to the rocking curve value. If crystal analyzer 30 is set for one-half of the maximum intensity, then small deviation angles will modulate the intensity above and below the half intensity values. The sensitivity to small deviation angles can be determined by a local slope of the rocking curve. The intensity I recorded in the image is the combination of such two effects, as shown below in Equation 1.

$$I = I_T \left( R + \frac{\partial R}{\partial \theta} \delta_Z \right) \qquad \text{Equation 1}$$

The intensity I is the diffracted beam intensity recorded on image plate 40. The intensity $I_T$ is the intensity which is transmitted through object 25. If imaged 325 alone, the intensity $I_T$ would be the normal absorption image of object 25. The reflectivity R of crystal analyzer 30 was set at approximately 0.5 for the one-half intensity point, according to experimentation conducted. The gradient term $\partial R/\partial \theta$ is the local slope of the rocking curve at a set position of crystal analyzer 30, and is used to determine an intensity modulation created by refraction of the x-rays along the z direction in object 25.

When the same object 25 is imaged at two settings of crystal analyzer 30, on each side of the rocking curve as shown in FIG. 2, Equations 2 and 3 are used to determine an intensity which is preferably recorded on each pixel of an image plate for each image acquired.

$$I_H = I_T\left(R_H + \left(\frac{\partial R}{\partial \theta}\right)_H \delta_Z\right) \quad \text{Equation 2}$$

$$I_L = I_T\left(R_L + \left(\frac{\partial R}{\partial \theta}\right)_L \delta_Z\right) \quad \text{Equation 3}$$

Intensities $I_L$ and $I_H$ correspond to low rocking curve angle and high rocking angle image pixel values, respectively. Equations 2 and 3 can be solved for the normal absorption image $I_T$ and the refraction angle image $\delta_Z$, as shown in Equations 4 and 5.

$$I_T = \frac{I_L\left(\frac{\partial R}{\partial \theta}\right)_H - I_H\left(\frac{\partial R}{\partial \theta}\right)_L}{R_L\left(\frac{\partial R}{\partial \theta}\right)_H - R_H\left(\frac{\partial R}{\partial \theta}\right)_L} \quad \text{Equation 4}$$

$$\delta_Z = \frac{I_L R_H - I_H R_L}{I_L\left(\frac{\partial R}{\partial \theta}\right)_H - I_H\left(\frac{\partial R}{\partial \theta}\right)_L} \quad \text{Equation 5}$$

Figure 7:
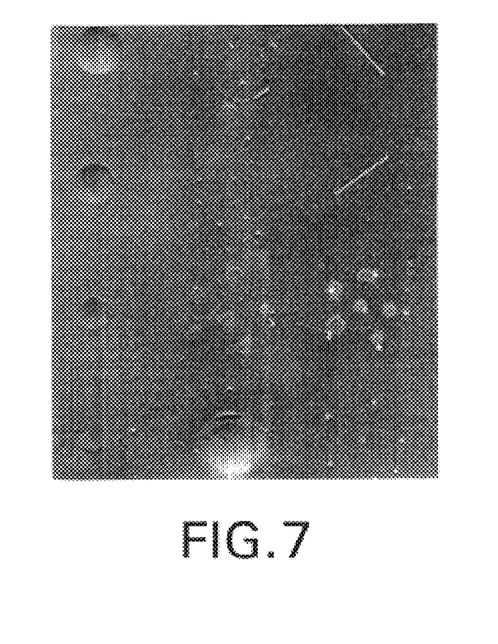
FIG. 7 is a photograph of the image of the same ACR phantom, showing a refraction angle image.
Figure 8:
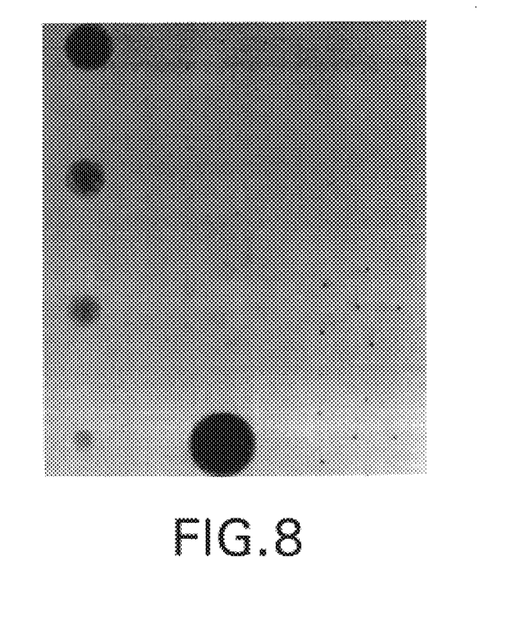
FIG. 8 is a photograph of the same ACR phantom image, showing an absorption image.

Equations 4 and 5 are used to compute and combine the low rocking curve angle image and the high rocking curve angle image, as shown in FIGS. 3 and 4, into refraction and absorption images, as shown in FIGS. 7 and 8. The algorithm is preferably applied on a pixel-by-pixel basis on raw data images which are aligned so that each pixel in each image is from a same region in imaged object 25.

Figure 9:
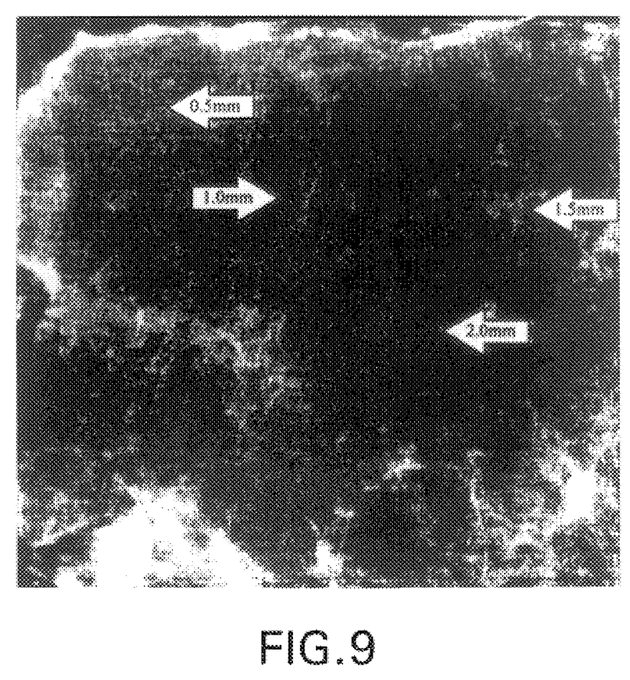
FIG. 9 is an enlarged photograph of breast tissue, using conventional x-ray image technology.
Figure 10:
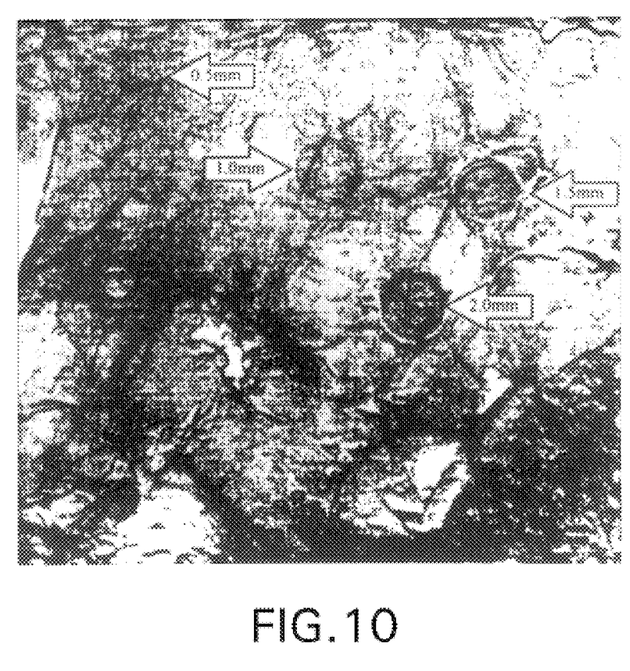
FIG. 10 is an enlarged photograph of the same breast tissue as shown in FIG. 9, but displaying an image taken according to the method of this invention.

FIGS. 9 and 10 show photographs of images taken of excised breast tissue from a patient that had undergone a mastectomy. FIG. 9 is an enlarged photograph of the breast tissue showing an image detected with a conventional mammography unit, a Siemens Mammomat II, as manufactured by Siemens Medical Systems, in Iselin, N.J., operated at 24 kVp. FIG. 10 shows a photograph of an image of the same breast tissue as that shown in FIG. 9, but using the XRI method according to this invention.

The analysis according to the XRI method of this invention assumes that refracted rays are traveling the same path through object 25 as would rays in the absence of refraction. Measured refraction angles in the ACR phantom have a maximum deviation value of approximately 0.2 microradians. In a 4.5 cm thick object 25, there would be a maximum lateral displacement of 9 nm at a backside of object 25. Thus the refracted rays and the non-refracted rays will travel very nearly the same path through object 25. Thus, there is justification for assuming that refraction does not affect transmitted beam 20 which passes through object 25. At the detector or image plate 40, according to one preferred embodiment of this invention, a maximum lateral displacement is less than approximately 2 μm due to the refraction effects. Because of the relatively small refraction angles, refraction should not produce a displaced beam at a detector location, which would result in image blurring, since a pixel dimension is about 0.1 mm.

An absorption image differs from a normal transmitted image according to conventional radiography technology which does not use a crystal analyzer, in that the absorption image contains nearly no scatter from imaged object 20, primarily due to extremely tight conditions imposed by a Bragg type scattering condition. Any rays which are deviated by even a few microradians from a direct path and/or which are deviated in energy by a few electron volts, such as $\Delta E/E \geq 10^{-4}$, will not be diffracted by crystal analyzer 30. Such arrangement will remove relatively small angle scattering and other forms of coherent scattering, and will also remove Compton scattering. Both types of scattering mechanisms contribute to loss of contrast in imaging. Thus, diffracted beam images are almost completely scatter-free. Such scatter-free property is important, for example, in allowing diffracted beam images to image tumor mass simulations, such as in the ACR phantom.

The ACR phantom is a relatively good example of a material having absorption and scatter wherein a sum in a normal transmission image almost completely destroys contrast of object 25, particularly when embedded in Lucite™ material. However, with analyzer system 10 according to this invention, the diffracted beam image removes scatter entirely and provides a contrast which is at least approximately 15 times the contrast in a normal transmission image obtained from conventional radiology methods. For example, the contrast of a 2.0 mm thick tumor, as simulated from a conventional synchrotron image, such as shown in FIG. 6, provides a measured contrast of 2.1% ΔI/I. The same tumor simulation, as shown in FIG. 8, taken with an XRI method according to this invention, gives a measured contrast of 36% ΔI/I. Such simulated tumor is a circular object in the upper left corner of the images.

The XRI method according to this invention can be conducted with either a Bragg type crystal analyzer 30 or a Laue type crystal analyzer 30. A Bragg type system uses reflection geometry to obtain refraction and absorption images in a near absence of coherent and inelastic scattering. Reflection geometry of the Bragg type system provides a single diffracted beam image at a single setting of crystal analyzer 30. An image produced with a Bragg system provides a refraction angle image of object 25 and a nearly scatter-free absorption image of object 25.

When using a Laue type system, as shown in FIG. 11, transmission geometry is used to obtain refraction and absorption images in the same manner as with a Bragg system. However, the Laue system has two main differences over the Bragg system. First, in a Laue system forward diffracted beam 37, as shown in FIG. 11, is emitted from crystal analyzer 30, in addition to diffracted beam 35. Forward diffracted beam 37 produces an image which contains some of the scatter rejected by the diffracted beam image. Information contained within the forward diffracted beam image can be used to detect and image scatter resulting from transmitted beam 20 passing through object 25. Second, the intensity of the image downstream of crystal analyzer 30 in a Laue system is not as intensity efficient as in a Bragg system. When crystal analyzer 30 has an optimal crystal thickness, diffracted beam 37 is approximately 10% of the beam intensity that it is when striking an entrance side of crystal analyzer 30. The efficiency of a Bragg system is approximately 50% or greater than the entrance beam intensity.

The Laue system provides a refraction angle image of object 25, a nearly scatter-free absorption image of object 25 and a scatter image of object 25. Forward diffracted beams 37 can be detected at each setting of the rocking curve, the low rocking curve angle and the high rocking curve angle. From such information, refraction and absorption effects can be determined and removed from the refraction image and the absolute absorption image to produce a nearly scatter-free image. Analyzer system 10 for a Laue system is basically the same as analyzer system 10 for a Bragg system, except that crystal analyzer 30 is a Laue type. As shown in FIG. 11, forward diffracted beam 37 passes through crystal analyzer 30. The crystal of crystal analyzer 30 preferably has the same material composition as the crystals of monochromator 11.

As shown in FIG. 11, an x-ray source is monochromated and collimated by double crystal monochromator 11. Depending upon the type of lattice planes for monochromator 11 and crystal analyzer 30, analyzer system 10 can have different sensitivity to refraction effects and rejection of scatter.

As shown in FIG. 11, x-ray beam 16 is monitored by ionization chamber 12 in order to maintain alignment of the double crystals of monochromator 11. Absorber 13 is used in combination with a scanning stage in order to set a skin entry dose which is delivered to object 25. Shutter 14 can be used to begin and end exposure. Ionization chamber 15 is preferably used to monitor a dose which is delivered to object 25.

In a preferred embodiment of this invention, object 25 and image plate 40 are scanned, preferably together, to produce a two-dimensional image. In another preferred embodiment of this invention, a digital detector which has a detector fixed with respect to x-ray beam 16 can be used to produce a two-dimensional image. It is possible for object 25 to remain fixed if the x-ray source, monochromator 11, ionization chambers 12 and 14, absorber 13 and shutter 14 are scanned together.

Figure 12:
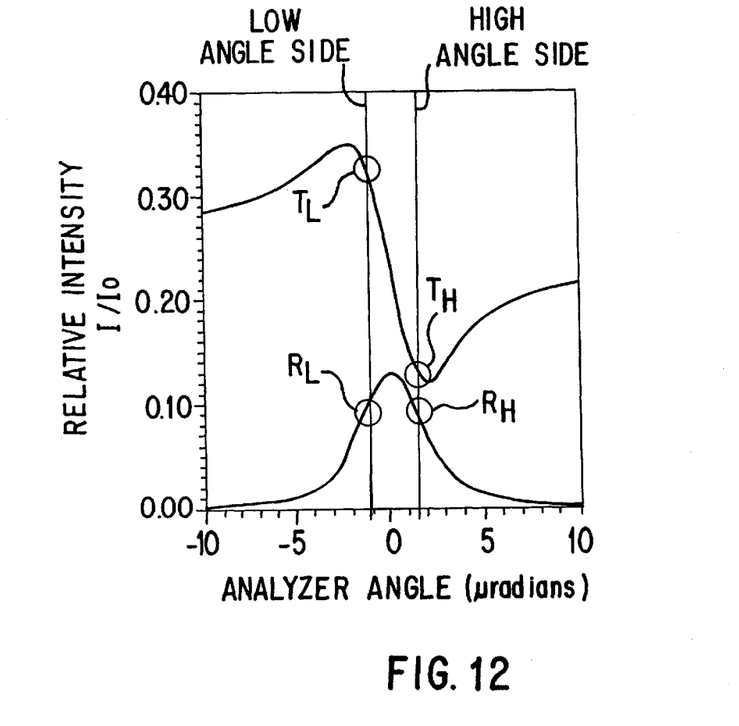
FIG. 12 is a graphical representation of an analyzer rocking curve for a silicon crystal Laue type analyzer having (3, 3, 3) lattice planes structure at an approximately 18 keV x-ray energy level.

FIG. 12 is a graphical representation of a rocking curve for a Laue type crystal analyzer 30, according to one preferred embodiment of this invention. The lower curve represents points for a diffracted beam and the upper curve represents points for a forward diffracted beam. FIG. 12 also shows vertical lines which define the low angle side and the high angle side of the rocking curve.

Figure 13:
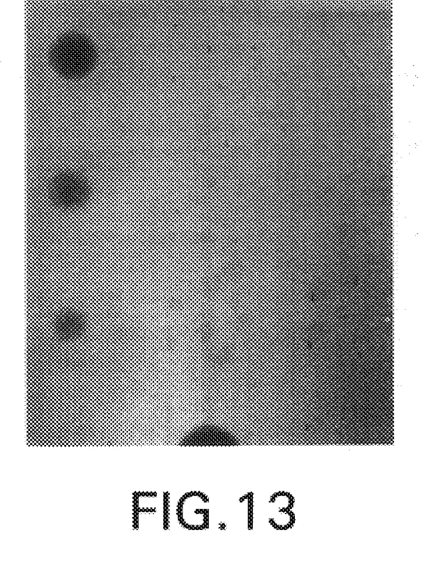
FIG. 13 is a photograph of an image of a diffracted beam image taken of the same ACR phantom, at a low rocking curve angle of the crystal analyzer.
Figure 14:
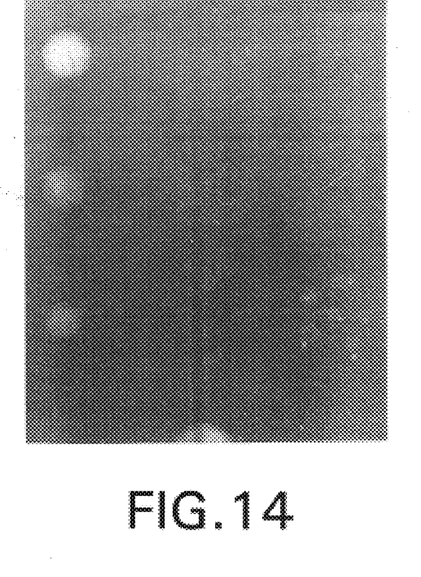
FIG. 14 is a photograph of a forward diffracted beam image taken of the same ACR phantom, at a low rocking curve angle of the crystal analyzer.
Figure 15:
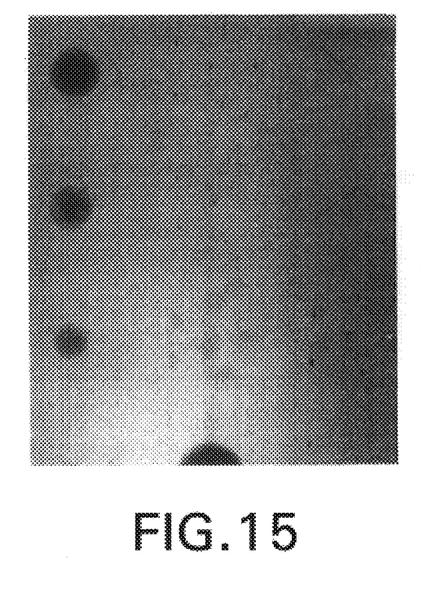
FIG. 15 is a photograph of a diffracted beam image taken of the same ACR phantom, at a high rocking curve angle of the crystal analyzer.
Figure 16:
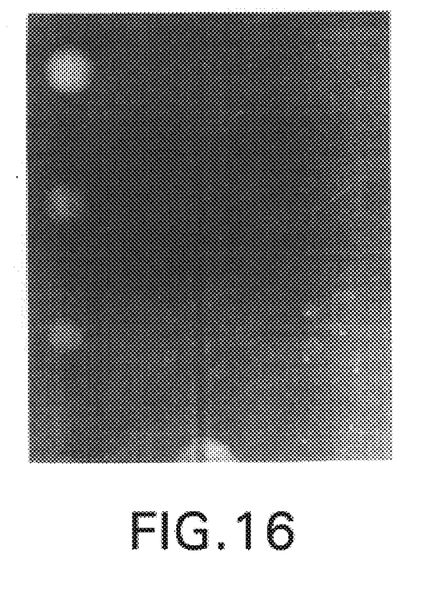
FIG. 16 is a photograph of a forward diffracted beam image taken of the same ACR phantom, at a high rocking curve angle of the crystal analyzer.

Two different images, diffracted beam image $I_R$ and forward diffracted beam image $I_T$, are taken at both the low rocking curve angle and the high rocking curve angle for a particular set up of analyzer system 10. Thus, crystal analyzer 30 is set to a low rocking curve angle position and raw images of diffracted beam image $I_{R(L)}$ and forward diffracted beam image $I_{T(L)}$, are acquired, as shown in FIGS. 13 and 14, respectively. The position of crystal analyzer 30 is then set to the high rocking curve angle and diffracted beam image $I_{R(H)}$ and forward diffracted beam image $I_{T(H)}$, are acquired, as shown in FIGS. 15 and 16, respectively. The particular order of acquiring the images at the low rocking curve angle and the high rocking curve angle is irrelevant.

Once the four images discussed in the preceding paragraph are acquired, the raw images are registered with each other, such as being lined up on a pixel-by-pixel basis. Diffracted beam images $I_{R(L)}$ and $I_{R(H)}$ are mathematically combined, on a pixel-by-pixel basis, using Equations 6 and 7 to solve for the refraction angle image $\delta_Z$ and the absorption image $I_A$.

$$\delta_Z = \frac{I_{R_L} R_H - I_{R_H} R_L}{I_{R_H}\left(\frac{\partial R}{\partial \theta}\right)_L - I_{R_L}\left(\frac{\partial R}{\partial \theta}\right)_H} \qquad \text{Equation 6}$$

$$I_A = \frac{I_{R_L}\left(\frac{\partial R}{\partial \theta}\right)_H - I_{R_H}\left(\frac{\partial R}{\partial \theta}\right)_H}{R_L\left(\frac{\partial R}{\partial \theta}\right)_H - R_H\left(\frac{\partial R}{\partial \theta}\right)_L} \qquad \text{Equation 7}$$

The forward diffracted beam image $I_{R(H)}$ and/or the forward diffracted beam image $I_{T(H)}$ are mathematically combined with the refraction angle image $\delta_Z$ and the absorption image $I_A$, using one of Equations 8, 9, or 10 to derive a scatter image $I_S$. Equation 10 represents an average of Equations 8 and 9 which are for the low rocking curve angle and the high rocking curve angle positions, respectively.

$$I_S = \frac{I_{T_L}}{T_\infty} - \left(T_L + \left(\frac{\partial T}{\partial \theta}\right)_L \delta_Z\right) I_A \qquad \text{Equation 8}$$

$$I_S = \frac{I_{T_H}}{T_\infty} - \left(T_H + \left(\frac{\partial T}{\partial \theta}\right)_H \delta_Z\right) I_A \qquad \text{Equation 9}$$

$$I_S = \frac{1}{2}\left[\frac{I_{T_H} + I_{T_L}}{T_\infty} - \left((T_L + T_H) + \left(\left(\frac{\partial T}{\partial \theta}\right)_L + \left(\frac{\partial T}{\partial \theta}\right)_H\right)\delta_Z\right) I_A\right] \qquad \text{Equation 10}$$

The intensity scale of the refraction angle image $\delta_Z$ is in units of angle, determined by the units of the slope of the rocking curve. The intensity scale of the absorption image $I_A$ is the same intensity units of the raw data images $I_L$ and $I_H$. The intensity scale of the scatter image $I_S$ is the same intensity units of the raw data images $I_{R(L)}$, $I_{T(L)}$, $I_{R(H)}$ and $I_{T(H)}$.

Equations 6 and 7 or 8 or 9 or 10 can be used to solve for diffracted beam image $I_{R(L)}$, forward diffracted beam $I_{T(L)}$ at the low rocking curve angle, and for diffracted beam image $I_{R(H)}$ and forward diffracted beam image $I_{T(H)}$ at the high rocking curve angle, using Equations 11–14, respectively.

$$I_{R_L} = \left(R_L + \left(\frac{\partial R}{\partial \theta}\right)_L \delta_Z\right) I_A \qquad \text{Equation 11}$$

$$I_{T_L} = \left(T_L + \left(\frac{\partial T}{\partial \theta}\right)_L \delta_Z\right) I_A + T_\infty I_S \qquad \text{Equation 12}$$

$$I_{R_H} = \left(R_H + \left(\frac{\partial R}{\partial \theta}\right)_H \delta_Z\right) I_A \qquad \text{Equation 13}$$

$$I_{T_H} = \left(T_H + \left(\frac{\partial T}{\partial \theta}\right)_H \delta_Z\right) I_A + T_\infty I_S \qquad \text{Equation 14}$$

When imaging at relatively high x-ray energies, reflection widths become relatively narrow and it is quite difficult to physically maintain alignment of monochromator 11 and/or crystal analyzer 30. Some horizontal banding in the images can be caused by misalignment. In one preferred embodiment according to this invention, analyzer system 10 may comprise a feedback system to maintain such alignment by varying the angular position of monochromator 11 and/or crystal analyzer 30.

The XRI method according to this invention can resolve refraction at any energy and thus will allow imaging at relatively higher x-ray energy levels. Thus a dose delivered to object 25 can be reduced while maintaining the same intensity to the detector.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. In a method for detecting an image of an object, wherein an x-ray beam is generated, the improvement comprising:

transmitting the x-ray beam through the object and emitting from the object a transmitted beam;

directing the transmitted beam at an angle of incidence upon a crystal analyzer;

detecting a first image of the object from a diffracted beam emitted from the crystal analyzer at a low rocking curve angle setting of the crystal analyzer;

detecting a second image of the object from a diffracted beam emitted from the crystal analyzer at a high rocking curve angle setting of the crystal analyzer; and combining the first image and the second image to derive a refraction image and an absolute absorption image of the object.

2. In a method according to claim 1 further comprising:

detecting a third image of the object from a forward diffracted beam image emitted from the crystal analyzer at the low rocking curve angle setting of the crystal analyzer;

detecting a fourth image of the object from a forward diffracted beam image emitted from the crystal analyzer at the high rocking curve angle setting of the crystal analyzer;

determining refraction and absorption effects of the forward diffracted beam at the low rocking curve angle setting and at the high rocking curve angle setting; and deriving a scatter image of isolated scatter by removing the refraction and absorption effects from the refraction image and the absolute absorption image.

3. In a method according to claim 2 wherein the crystal analyzer upon which the transmitted beams are directed is a Laue type analyzer.

4. In a method according to claim 1 wherein the first image and the second image are exposed on a detector capable of producing a digitized image.

5. In a method according to claim 4 wherein the exposed first image and the exposed second image are digitized.

6. In a method according to claim 5 wherein the digitized images are mathematically combined to form a digitized refraction image and a digitized absolute absorption image.

7. In a method according to claim 6 wherein the digitized actual image is converted to a visual actual image.

8. In a method according to claim 1 wherein the crystal analyzer upon which the transmitted beams are directed is a Bragg type analyzer.

9. In a method according to claim 1 wherein the transmitted beam has an energy level in a range of approximately 16 keV to approximately 25 keV.

10. In a method according to claim 1 wherein the transmitted beam is generated, upstream from the object, from monochromator crystals constructed of silicon with (3, 3, 3) lattice planes.

11. In a method according to claim 1 further comprising increasing a relative intensity of the image of the object by adjusting an angular position of the crystal analyzer.

12. In a method according to claim 11 wherein the angular position of the crystal analyzer is adjusted to be within a rocking curve of the crystal analyzer.

13. In a method according to claim 11 wherein the angular position of the crystal analyzer is adjusted in steps of approximately 1 microradian increments.

14. In a method according to claim 1 wherein a first intensity $(I_L)$ of the combined image of the object is determined at a low rocking curve angle and a second intensity $(I_H)$ of the combined image is determined at a high rocking curve angle.

15. In a method according to claim 14 wherein the first intensity $(I_L)$ and the second intensity $(I_H)$ are used to determine a normal absorption image $(I_T)$ and a refraction angle image $(\delta_Z)$ of the object.

16. In a method according to claim 15 wherein the normal absorption image $(I_T)$ is determined by:

$$I_T = \frac{\left(I_L\left(\frac{\partial R}{\partial \theta}\right)\right)_H - \left(I_H\left(\frac{\partial R}{\partial \theta}\right)\right)_L}{\left(R_L\left(\frac{\partial R}{\partial \theta}\right)\right)_H - \left(R_H\left(\frac{\partial R}{\partial \theta}\right)\right)_L}$$

wherein $R_L$ and $R_H$ respectively represent low rocking curve and high rocking curve reflect ivies.

17. In a method according to claim 15 wherein the refraction angle image $(\delta_Z)$ is determined by:

$$\delta_Z = \frac{I_L R_H - I_H R_L}{\left(I_L\left(\frac{\partial R}{\partial \theta}\right)\right)_H - \left(I_H\left(\frac{\partial R}{\partial \theta}\right)\right)_L}$$

where $R_L$ and $R_H$ respectively represent low rocking curve and high rocking curve reflect ivies.

18. In a method according to claim 15 wherein the combined image at the low rocking angle curve and the combined image at the high rocking curve angle are aligned so that each pixel of each of the combined images is from a same region of the object, and the normal absorption image $(I_T)$ and the refraction angle image $(\delta_Z)$ are determined on a pixel-by-pixel basis.

19. In a method according to claim 1 wherein the x-ray beam is a mono-energetic synchrotron beam.

* * * * *